(12) United States Patent
Csikòs et al.

(10) Patent No.: US 6,220,752 B1
(45) Date of Patent: Apr. 24, 2001

(54) X-RAY EXAMINATION APPARATUS

(75) Inventors: Jaǹos Csikòs; György Medgyesi; Attila Barnavàri, all of Budapest (HU)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/425,654

(22) Filed: Oct. 22, 1999

(30) Foreign Application Priority Data

Oct. 24, 1998 (DE) ............................................... 198 49 091

(51) Int. Cl.$^7$ ....................................................... H05G 1/02
(52) U.S. Cl. ............................................. 378/197; 378/196
(58) Field of Search ................................... 378/197, 196, 378/198, 193, 195

(56) References Cited

U.S. PATENT DOCUMENTS

| | | | |
|---|---|---|---|
| 5,014,292 | * 5/1991 | Siczek | 378/196 |
| 5,023,899 | * 6/1991 | Ohlson | 378/196 |
| 5,751,788 | * 5/1998 | Khutoryansky | 378/197 |
| 5,829,076 | * 11/1998 | Csikos et al. | 5/601 |

* cited by examiner

Primary Examiner—Robert H. Kim
Assistant Examiner—Irakli Kiknadze
(74) Attorney, Agent, or Firm—John F. Vodopia

(57) ABSTRACT

The invention relates to an X-ray examination apparatus which includes a patient table (1), a fluoroscopy image intensifier (61) which is displaceable in the longitudinal direction of the table on a first carriage (6), an overtable X-ray source (2) which is aligned with respect thereto and is coupled to the first carriage, and an image recording means (71) which is displaceable on a second carriage (7). The second carriage can quickly move to a parking position and from this parking position to an exposure position in that the second carriage is displaceable in the longitudinal direction of the table, independently of the first carriage, and in that there is provided a drive system (8,9) which displaces the two carriages in synchronism in a first mode of operation and displaces the second carriage relative to the first carriage in a second mode of operation.

8 Claims, 1 Drawing Sheet

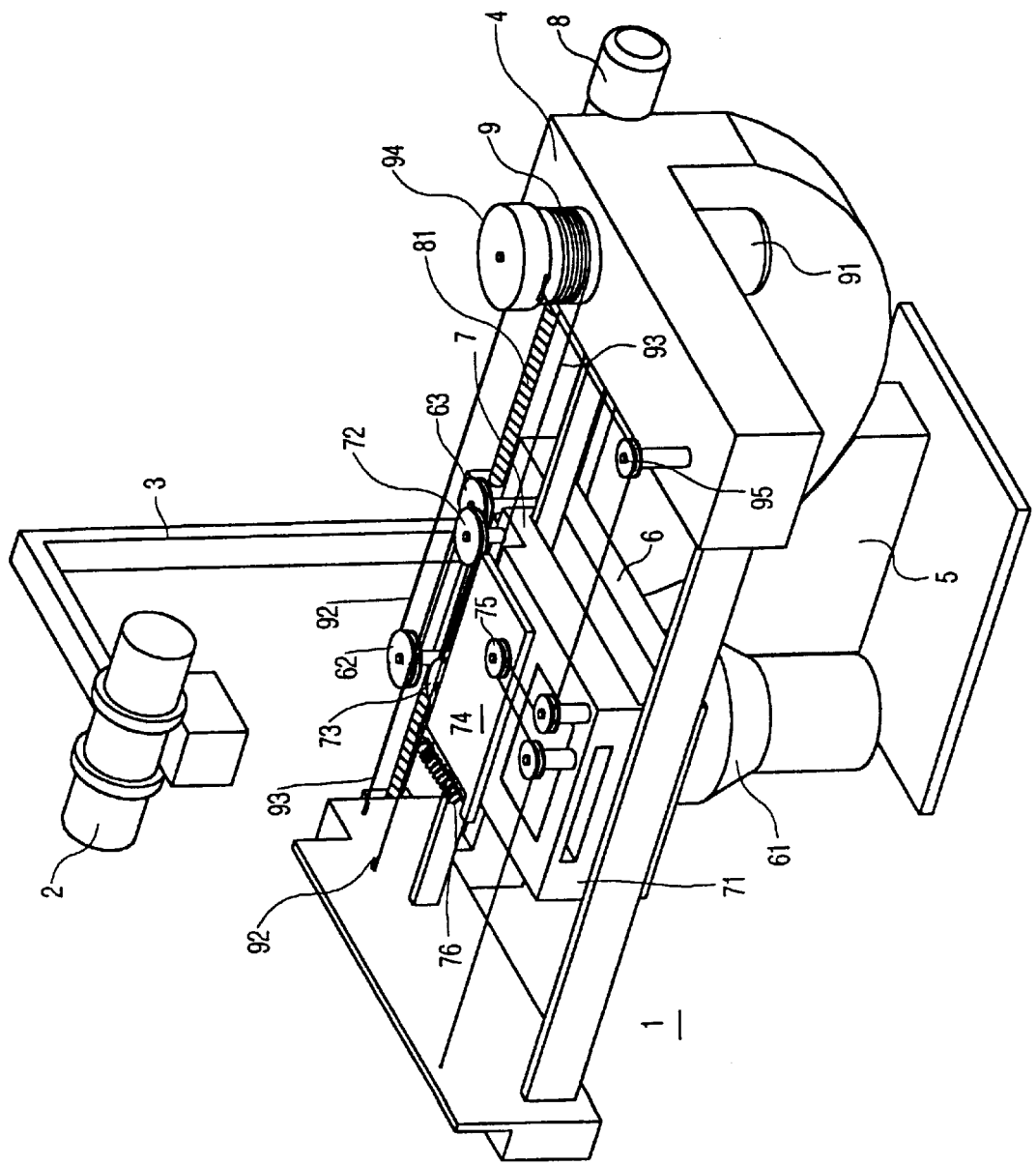

X-RAY EXAMINATION APPARATUS

BACKGROUND OF THE INVENTION

1. Field of the Invention

The invention relates to an X-ray examination apparatus which includes a patient table, a fluoroscopy image intensifier which is mounted on a first carriage so as to be displaceable in the longitudinal direction of the table, an overtable X-ray source which is aligned with respect to said intensifier and is coupled to the first carriage, and an image recording means which is displaceable on a second carriage.

2. Description of Related Art

Known apparatus of this kind usually include an X-ray image intensifier which serves as the fluoroscopy image intensifier and a moving grid for receiving a film cassette as the image recording device. This necessitates a very fast change over between image recording and X-ray fluoroscopy. During an exposure, the moving grid with the film cassette is situated between the X-ray image intensifier and the X-ray source. During fluoroscopy, however, the film cassette must be moved out of the beam path of the X-ray tube to a parking position. To this end, known X-ray examination apparatus of the kind set forth include a first carriage which is displaceable in the longitudinal direction of the table and carries an X-ray image intensifier and a spot film device within which a second carriage with the film cassette can be displaced perpendicularly to the longitudinal direction of the table. A spot film device of this kind is intricate and makes it necessary for the X-ray examination apparatus to be wide enough so as to enable lateral displacement of the second carriage to the parking position.

Citation of a reference herein, or throughout this specification, is not to construed as an admission that such reference is prior art to the Applicants' invention of the invention subsequently claimed.

SUMMARY OF THE INVENTION

It is an object of the present invention to realize, while using simple means, an X-ray examination apparatus of the kind set forth which has a compact construction. This object is achieved according to the invention in that the second carriage is displaceable in the longitudinal direction of the table, independently of the first carriage, and that there is provided a drive system which displaces the two carriages in synchronism in a first mode of operation and displaces the second carriage relative to the first carriage in a second mode of operation.

According to the invention, the second carriage is displaceable in the longitudinal direction of the table, independently of the first carriage, i.e. with respect to the recording position, the parking position is shifted in the longitudinal direction of the table so that the lateral dimensions of the X-ray examination apparatus are not increased. In the first mode of operation the two carriages are displaced in synchronism with one another, the second carriage remaining in a defined position relative to the first carriage, for example in a parking position directly adjacent the first carriage. In order to perform an X-ray exposure, only a comparatively small displacement of the second carriage will then be required in the second mode of operation, irrespective of the position of the first carriage.

The drive system could be realized, for example by way of two spindle drives operative in the longitudinal direction of the table. In the first drive mode the two spindle drives would operate in synchronism, thus driving also the two carriages in synchronism, whereas in the second mode of operation one spindle drive is stationary and the second spindle drive is active and displaces the second carriage. In describes an even simpler construction, the drive system further comprises a drive which is active in the first mode of operation so as to displace the first carriage, and wherein the apparatus further comprises a first drum which rotates in the second mode of operation, and at least one pulling means which can be wound onto and from the first drum and is guided, via guide means on the first and the second carriage, in a first and a second loop, said pulling means being attached at one end of the patient table, the length of the loops changing in opposite directions upon rotation of the first drum. In this context an oppositely directed change of the loop length is to be understood to mean that the length of one loop increases when the length of the other loop decreases and vice versa. When the drive for the first carriage is stationary and the drum rotates (second mode of operation), one loop becomes shorter and the other loop becomes longer, the guide means on the second carriage then displacing this carriage relative to the first carriage. However, when the first carriage is displaced by the drive in the first mode of operation and the drum is stationary, the second carriage cannot be displaced relative to the first carriage, because for such a displacement one of the two loops would have to become longer; however, this is impossible in the stationary condition of the drum.

The embodiment wherein the first drum on the one side and the pulling means on the other side are attached to opposite ends of the patient table, viewed in the longitudinal direction, enables examination of a patient in the entire region between the two ends of the frame, i.e. the fluoroscopy image intensifier can be displaced from the head end to the foot end.

In principle there could be provided two pulling means whose ends are connected to the drum and which are wound onto this drum in opposite directions, so that one pulling means would be wound onto the drum while the other is unwound therefrom during rotation of the drum. In simpler embodiment, there is provided only a single pulling means whose ends are connected to the patient table via the loops, the central part of said pulling means being wound on and attached to the first drum. The embodiment wherein the ends of the pulling means are guided via respective guide means on the first and the second carriage, wherein the sum of the diameters of the guide means corresponds to the diameter of the first drum, and wherein the ends of the pulling means are guided in such a manner that outside the guide means a parallel trajectory is obtained in the longitudinal direction of the table that outside the guide pulley the pulling means extends parallel to the longitudinal direction of the table everywhere.

In an X-ray examination apparatus in which the image recording means is displaced transversely of the longitudinal direction of the table in a spot film device, the image recording means can be shielded from scattered radiation, produced before and after the exposure during fluoroscopy, by means of a shield which is rigidly connected to the spot film device and is impervious to X-rays. In an apparatus in which the parking position is shifted in the longitudinal direction of the table, a stationary shield cannot shield the image recording means in the parking position from the scattered radiation produced during fluoroscopy, because such a shield would constrict the zone in which fluoroscopy or image recording is possible. The embodiment further comprising a scattered radiation shield which is mounted on the second carriage and which is displaceable in the direction transversely to the longitudinal direction of the table and is coupled to the drive system in such a manner that it shields the image recording means when the second carriage is centered with respect to the first carriage, and which leaves the image recording means free when the second carriage is in a parking position to the side of the first carriage provides shielding from scattered radiation by means of a scattered radiation shield which is displaceable transversely of the longitudinal direction of the table.

Without utilizing a separate drive for the scattered radiation shield, in a further embodiment further comprising a second drum which is coupled to the first drum and on which there can be wound a pulling means which is guided in a loop via guide means on the second carriage and on the scattered radiation shield and is connected to the frame in such a manner that the length of the loop is greatest when the second carriage is aligned with respect to the first carriage, the length of the loop being shorter when the second carriage is in a parking position, it is achieved that the scattered radiation shield shields the image recording means whenever it is situated in a parking position and releases it whenever it is in the recording position and when it is aligned with respect to the fluoroscopy image intensifier.

A patient table which is constructed according to the invention as part of an X-ray examination apparatus comprises a first carriage which is displaceable in the longitudinal direction of the table, an overtable X-ray source coupled to the first carriage, and on which a flouroscopy image converter mounted on the first carriage, and an image recording means which is displaceable on a second carriage, and a drive system which displaces the two carriages in synchronism in a first mode of operation and displaces the second carriage relative to the first carriage in a second mode of operation wherein the second carriage is displaceble in the longitudinal direction of the table, independently of the first carriage.

BRIEF DESCRIPTION OF THE DRAWING

The invention will be described in detail hereinafter with reference to the drawing.

DETAILED DESCRIPTION OF THE PREFERRED EMBODIMENT

The X-ray examination apparatus includes a patient table 1 and an X-ray source 2 which is mounted on a stand 3 which is displaceable in the longitudinal direction of the table and is mounted above the patient table 1; therefore, it is also referred to as an overtable X-ray source. The patient table 1 is shown without a table top, so that the components situated underneath the table can be seen.

The patient table includes a frame 4 which is mounted on a table base 5 so as to be pivotable about a horizontal axis so that it can be pivoted from the horizontal position shown to an inclined position or a vertical position. A first carriage 6 is mounted on the frame 4 so as to be displaceable in the longitudinal direction of the table. This carriage supports an X-ray image intensifier 61. Above the first carriage there is situated a second carriage 7 which is also displaceable in the longitudinal direction of the table, independently of the first carriage. The second carriage is provided with a moving grid 71 with a slit for the introduction or removal of a film cassette.

Via a drive spindle 81, the first carriage 6 can be displaced by a first motor 8. Because the carriage 6 is coupled to the stand 3, the X-ray source 2 is taken along so that it always remains aligned with respect to the first carriage 6 or the X-ray image intensifier 61 situated therebelow. The second carriage 7 can be displaced from its recording position which is shown in the drawing and is centered with respect to the image intensifier 61 or the X-ray source 2, to a parking position (and back) by means of a drum 9 which is mounted at the foot end of the frame 4 and is driven by a drive motor 91.

A wire rope whose center is secured to the drum 9 is wound onto the drum 9. The upper straight end 92 of the rope is connected, via a first pulley 62, to the left-hand side (remote from the drum 9) of the carriage 6 and, via a pulley 72 which is mounted at the right-hand side (facing the drum 9) of the carriage 7, to the head end of the frame 4 whereto it is attached. The second (lower) end 93 of the rope is guided, via a second pulley 73 on the left-hand side of the second carriage 7 and a second pulley 63 on the right-hand side of the first carriage, to the head end of the frame whereto it is also attached.

Because the rope ends are guided via the pulleys, each rope end forms an S-shaped loop. However, because the second rope end 93 (as opposed to the first rope end 92) is first guided via a pulley (73) on the second carriage and after that via a pulley (63) on the first carriage, this S-shape is the mirror image of the S-shape formed by the first rope end 92. Consequently, the lengths of the loops can change only in the opposite sense, i.e. in the case of a displacement of the second carriage relative to the first carriage the length of one loop is reduced while that of the other loop is increased.

When the drum 9 is driven clock-wise, the rope end 92, and the loop formed thereby, becomes shorter whereas the length of the rope end 93 (and the loop formed thereby) is increased. Consequently, the second carriage is displaced, relative to the first carriage 6, in the direction of the head end. When the motor 91 drives the drum 9 in the counter clock-wise direction, exactly the opposite situation occurs: the length of the rope end 93 and its loop become shorter whereas the length of the cable end 92 and its loop increases. The second carriage 7 is then pulled, relative to the first carriage, in the direction of the foot end. Because the second carriage can thus be displaced, relative to the first carriage, in the direction of the foot end as well as in the direction of the head end, the second carriage can be displaced to a parking position at the head end when the first carriage is nearer to the foot end and to a parking position at the foot end when the first carriage is nearer to the head end. This enables displacement of the image intensifier and the X-ray source throughout the region between the two frame ends, thus enabling examination of a patient over substantially the entire length of the patient, without it being necessary to displace the table top (not shown) on which the patient is accommodated.

When the motor 8 drives the first carriage 6 and the drum 9 is stationary, because rotation is blocked by the motor 91, the carriage 6 is displaced. Because of the blocked condition of the drum 9, the length of the rope ends 92, 93 does not change and the length of the loops formed by these rope ends cannot change either, so that the second carriage 7 follows the first carriage 6, the loops of the rope ends being displaced together with the two carriages 6, 7. This holds when the carriage 7 is centered with respect to the image intensifier (as shown in the drawing) and also when it is situated in a parking position.

The two carriages thus move in synchronism when driven by the motor 8 while the motor 91 is stationary, i.e. the carriages do not change position relative to one another (first mode of operation). In the case of driving by the motor 91 while the motor 8 is stationary, however, only the second carriage 7 moves relative to the first carriage 6 (second mode of operation).

An advantage of the X-ray apparatus according to the invention (compared to an X-ray apparatus with a spot film device which is rigidly coupled to the image intensifier carriage) resides in the fact that the second carriage 7 has its own guide on the frame 4 and hence need not be supported by the first carriage. Therefore, the carriage 6 may have a comparatively light and compact construction. Another advantage resides in the fact that the drive motors 8, 91 are mounted on the frame and not on one of the carriages 6 or 7.

When the carriage 7, and hence the moving grid 71, is located in a parking position in which they vacate the beam path to the image intensifier 61, there is a risk that a film cassette present in the moving grid is exposed to scattered radiation produced in the patient during fluoroscopy. This scattered radiation can be absorbed by a scattered radiation shield 74 which is impervious to the X-rays, is carried along by the carriage 7, above the moving grid 71, and shields a film 71 in the moving grid in the parking positions, but leaves it free in the exposure position shown.

In order to displace the scattered radiation shield, an auxiliary drum 94 is mounted on the drive shaft of the drum 9, said auxiliary drum 94 being provided with a slit (not shown) in which a wire rope 95 is clamped. This rope is guided, via a pulley 95' on the frame 4, a first pulley on the moving grid 71, a pulley 75 which is connected to the shield 74, and a second pulley on the moving grid, to the head end of the frame 4 where it is attached.

The rope 95 is fully unwound from the auxiliary drum 94 when the drum 9 occupies a position in which the second carriage 7 is centered with respect to the first carriage 6. The scattered radiation shield 74 is then laterally pulled out of the beam path of the X-ray source 2 by a tension spring 76 (i.e. perpendicularly to the longitudinal direction of the table), so that an X-ray exposure can take place. In order to displace the carriage 7 to a parking position, the drum 9 is rotated, and hence also the auxiliary drum 94, the rope 95 then being wound onto the auxiliary drum either clock-wise or counter clock-wise. The length of the loop around the pulley 75 on the scattered radiation shield 74 is then reduced, so that this shield is pulled, against the force of the spring 76, into the beam path in the direction perpendicular to the longitudinal direction of the table, so that it can shield a film cassette present in the moving grid 71 from scattered radiation.

The position of the first carriage 6 can be determined by means of an electrical sensor which is coupled to the motor 8. Analogously, the position of the second carriage 7 relative to the first carriage 6 can be determined by means of an electrical sensor which is coupled to the drive motor 91. This enables the second carriage 7 to be moved to the parking position in which it cannot obstruct the displacement of the first carriage in the direction of the respective nearest end of the frame. In addition to the described two operating modes, in which each time only one of the two motors 8, 91 is active, there may be provided a further operating mode in which both motors are simultaneously active. In that case the first carriage 6 will be displaced relative to the frame 4 while at the same time the second carriage 7 is displaced relative to the first carriage.

All references cited herein are incorporated herein by reference in their entirety and for all purposes to the same extent as if each individual publication or patent application was specifically and individually indicated to be incorporated by reference in its entirety for all purposes.

What is claimed is:

1. An X-ray examination apparatus comprising:
   a patient table,
   a fluoroscopy image intensifier which is mounted on a first carriage so as to be displaceable in the longitudinal direction of the table,
   an overtable X-ray source which is aligned with respect to said intensifier and is coupled to the first carriage,
   an image recording means which is displaceable on a second carriage, and
   a drive system which displaces the two carriages in synchronism in a first mode of operation and displaces the second carriage relative to the first carriage in a second mode of operation wherein the second carriage is displaceable in the longitudinal direction of the table, independently of the first carriage.

2. An X-ray examination apparatus as claimed in claim 1, wherein the drive system further comprises a drive which is active in the first mode of operation so as to displace the first carriage, and
   wherein the apparatus further comprises a first drum which rotates in the second mode of operation, and at least one pulling means which can be wound onto and from the first drum and is guided, via guide means on the first and the second carriage, in a first and a second loop, said pulling means being attached at one end of the patient table, the length of the loops changing in opposite directions upon rotation of the first drum.

3. An X-ray examination apparatus as claimed in claim 1, further comprising a scattered radiation shield which is mounted on the second carriage and which is displaceable in the direction transversely to the longitudinal direction of the table and is coupled to the drive system in such a manner that it shields the image recording means when the second carriage is centered with respect to the first carriage, and which leaves the image recording means free when the second carriage is in a parking position to the side of the first carriage.

4. An X-ray examination apparatus as claimed in claim 2, wherein the first drum on the one side and the pulling means on the other side are attached to opposite ends of the patient table, viewed in the longitudinal direction.

5. An X-ray examination apparatus as claimed in claim 2, wherein the at least one pulling means is a single pulling means whose ends are connected to the patient table via the loops, the central part of said pulling means being wound on and attached to the first drum.

6. An X-ray examination apparatus as claimed in claim 5, wherein the ends of the pulling means are guided via respective guide means on the first and the second carriage, wherein the sum of the diameters of the guide means corresponds to the diameter of the first drum, and wherein the ends of the pulling means are guided in such a manner that outside the guide means a parallel trajectory is obtained in the longitudinal direction of the table.

7. An X-ray examination apparatus as claimed in claim 3, further comprising a second drum which is coupled to the first drum and on which there can be wound a pulling means which is guided in a loop via guide means on the second carriage and on the scattered radiation shield and is connected to the frame in such a manner that the length of the loop is greatest when the second carriage is aligned with respect to the first carriage, the length of the loop being shorter when the second carriage is in a parking position.

8. A patient table for an X-ray examination apparatus, comprising:
   a first carriage which is displaceable in the longitudinal direction of the table,
   an overtable X-ray source coupled to the first carriage, and
   a fluoroscopy image converter mounted on the first carriage, and
   an image recording means which is displaceable on a second carriage, and
   a drive system which displaces the two carriages in synchronism in a first mode of operation and displaces the second carriage relative to the first carriage in a second mode of operation wherein the second carriage is displaceable in the longitudinal direction of the table, independently of the first carriage.

* * * * *